United States Patent [19]

Chao

[11] 4,079,048

[45] Mar. 14, 1978

[54] PROCESS FOR PREPARING FUNCTIONAL YEAST PROTEINS USING ALKALINE CONDITIONS

[75] Inventor: Kwei C. Chao, Naperville, Ill.

[73] Assignee: Standard Oil Company (Indiana), Chicago, Ill.

[21] Appl. No.: 722,050

[22] Filed: Sep. 10, 1976

[51] Int. Cl.$^2$ .............................................. A23J 1/18
[52] U.S. Cl. .............................. 260/112 R; 426/564; 426/590; 426/568; 426/656
[58] Field of Search .................................... 260/112 R

[56] References Cited

U.S. PATENT DOCUMENTS

| 3,718,541 | 2/1973 | Kalina | 260/112 X |
| 3,725,075 | 4/1973 | Muroi et al. | 260/112 X |
| 3,862,112 | 1/1975 | Ishida et al. | 260/112 |
| 3,867,555 | 2/1975 | Newell et al. | 260/112 X |
| 4,005,062 | 1/1977 | Schnell | 260/112 R |

FOREIGN PATENT DOCUMENTS 1,322,160  7/1973  United Kingdom.

Primary Examiner—Howard E. Schain
Attorney, Agent, or Firm—Gregory E. Croft; Arthur G. Gilkes; William T. McClain

[57] ABSTRACT

Functional yeast protein products with good thermogelability, emulsification capacity, foaming ability, solubility, and whippability are prepared by an alkali extraction of whole yeast cells preceded by a hot water extraction and/or a dilute alkaline extraction. These products are good substitutes for either casein, sodium caseinate, or egg white, and can also be used in making stabilized acidic protein beverages.

24 Claims, No Drawings

PROCESS FOR PREPARING FUNCTIONAL YEAST PROTEINS USING ALKALINE CONDITIONS

BACKGROUND OF THE INVENTION

1. Field of the Invention

This invention relates to processes for preparing yeast food products. More particularly, it relates to an alkaline extraction process for preparing yeast whippable proteins and/or acid-soluble proteins.

2. Description of the Prior Art

Protein ingredients such as egg white, casein, sodium caseinate, and dried milk solids, are useful in food applications primarily because of their functional properties such as whippability, emulsification capacity, gelability, solubility, etc. Unfortunately, they are expensive and in short supply. Yeast materials, especially those processed products having a bland flavor and reduced purine content, have the potential to replace some of these protein ingredients in various food applications. It is necessary, however, to efficiently extract the proteins from the yeast cell and process them properly to obtain the desired functional properties.

One method of removing the proteins from the yeast cells is by alkaline extraction. An example of this process is provided in U.S. Pat. No. 3,862,112. The efficiency of such a process is determined generally by the combined effect of alkalinity, reaction temperature, reaction time, and to a certain extent the cellular material concentration. Both the yield and the functional properties of the recovered protein are closely related, and after digestion in the hot alkali solution, the processed yeast material contains a complex mixture of various cellular components and hydrolysis products in both soluble and insoluble forms. These various materials greatly affect the quality of the protein product in terms of composition and functional properties.

Accordingly, it is an object of this invention to develop a process for preparing functional yeast proteins.

It is a further object of this invention to produce a yeast whippable protein.

These and other objects will become apparent upon further reading of this specification.

SUMMARY OF THE INVENTION

In one aspect, the invention resides in a process for preparing functional food yeast proteins comprising: heating an aqueous slurry of whole yeast cells to an elevated temperature to remove undesirable flavor and color bodies; separating the yeast cells from the aqueous extract; slurrying the separated yeast cells with a dilute alkaline solution at an elevated temperature to remove nucleotidic materials; separating the yeast cells from the alkaline extract; reslurrying the separated yeast cells in a solution of strong alkali at an elevated temperature to extract the proteins; neutralizing the slurry; separating the undigested cell residue from the supernatant containing the extracted protein; acidifying the supernatant, preferably to a pH of from about 3.5 to 4.5, to precipitate proteins at the isoelectric point from the mother liquor solution containing soluble proteins; neutralizing the mother liquor solution; and drying the mother liquor solution to yield a yeast whippable protein. As a coproduct, a yeast protein isolate can be produced by neutralizing and drying the isoelectrically precipitated proteins. Optionally, the isoelectrically precipitated proteins can be washed with a solvent such as water, ethanol, or acetone prior to drying to improve the flavor characteristics of the yeast protein isolate product. Also, the undigested cell residue separated after neutralization of the slurry can be washed with water if desired and the wash water returned to the process by combination with the supernatant prior to acidification.

More specifically, the invention resides in a process for preparing functional food yeast proteins comprising: heating an aqueous slurry of whole yeast cells to a temperature of from 60° to 100° C., preferably about 90° to 95° C. for from 1 to 5 minutes to extract flavor and color bodies; separating the yeast cells from the aqueous extract; slurrying the separated yeast cells in a dilute alkaline solution having a pH of from 8.5 to 10.0, preferably about 9.5, at a temperature of from 85° to 95° C., preferably about 90° C. for about 10 minutes to extract nucleotidic materials; separating the yeast cells from the resulting alkaline extract; reslurrying the separated yeast cells in a solution of from 0.1 to 0.3N sodium hydroxide or potassium hydroxide, preferably 0.15N sodium hydroxide, at a temperature of from 85° to 100° C., preferably about 95° C. for about 30 minutes; neutralizing the slurry; separating the undigested cell residue from the supernatant which contains the extracted proteins; acidifying the supernatant to a pH of from about 3.5 to 4.5, preferably about 4.0, to precipitate the isoelectrically precipitable proteins; separating the precipitated proteins from the mother liquor solution containing the soluble proteins; neutralizing the mother liquor solution to a pH of from 6.7 to 7.5, preferably 7.0; and spray-drying the mother liquor solution to yield a yeast whippable protein. The precipitated proteins can be neutralized, dissolved in water, and spray-dried to yield a yeast protein isolate coproduct. Optionally, the precipitated proteins can be washed with a solvent such as water, ethanol, or acetone prior to dissolution in water for spray-drying. Also, as previously mentioned, the undigested cell residue can be washed with water.

In another aspect, the invention resides in a similar process for preparing functional food yeast proteins, but without the initial hot water extraction step. The process comprises the steps of: slurrying whole yeast cells in a dilute alkaline solution, preferably having a pH of from 8.5 to 10.0, at an elevated temperature, preferably from 85 to 95° C., to extract both nucleotidic materials and undesirable flavor and color bodies; separating the yeast cells from the alkaline extract; reslurrying the separated yeast cells in a solution of strong alkali, preferably from 0.1 to 0.3N sodium hydroxide, at an elevated temperature, preferably from 85 to 100° C., to extract proteins; neutralizing the slurry; separating the undigested cell residue from the supernatant containing the extracted proteins; acidifying the supernatant, preferably to a pH of from about 3.5 to 4.5, to precipitate the isoelectrically precipitable proteins; separating the precipitated proteins from the mother liquor solution which contains the soluble proteins; neutralizing the mother liquor solution; and drying the mother liquor solution to yield a yeast whippable protein. (The conditions described for previous aspects of this invention are also applicable to this aspect of the invention insofar as the steps are the same). By eliminating the hot water extraction step, the process is somewhat simplified and a by-product (aqueous extract) is eliminated. On the other hand, the single extract does not contain the B-vitamins present in the aqueous extract because they are decomposed when exposed to hot alkaline solutions.

Therefore, in choosing between the two processes, it is necessary to consider the end use of the extract(s) obtained, which include such uses as flavorants and food or nutritional supplements.

In a further aspect, the invention resides in the products produced by the aforementioned processes.

All aspects of this invention are applicable to food yeasts in general, and more particularly, to those yeasts selected from the group consisting of *Candida utilis, Saccharomyces cerevisiae, Saccharomyces fragilis,* and *Saccharomyces carlsbergensis.*

DESCRIPTION OF THE PREFERRED EMBODIMENT

A culture of *Candida utilis* yeast cells (ATCC-9256) was grown on an ethanol substrate under oxygen-limiting growth conditions. The whole cells were harvested and concentrated into a 10–14 weight percent (dry weight) aqueous slurry or cream. The aqueous slurry was heated to a temperature of 90° C. for about 5 minutes to remove materials which would give the product poor color and flavor characteristics. The slurry was centrifuged to separate the aqueous extract from the cells, which were reslurried into a 10 weight percent suspension with a dilute alkaline solution of 0.03N sodium hydroxide having a pH of 9.5. The alkaline slurry was heated to a temperature of about 90° C. for about 10 minutes to extract primarily nucleotidic materials. The slurry was centrifuged to separate the alkaline extract from the cells. The separated cells were then reslurried in a 0.15N sodium hydroxide solution at a temperature of about 95° C. for about 30 minutes to extract the proteinaceous materials. Thereafter, the slurry was neutralized to lower the viscosity and the undigested cell residue was separated from the supernatant by centrifugation. The supernatant containing the extracted proteins was acidified to a pH of 4.2 to precipitate the isoelectrically precipitable proteins, which were separated from the mother liquor solution or whey by centrifugation. The mother liquor solution was then neutralized to about pH 7.0 and spray-dried to yield a yeast whippable protein. Also, the precipitated portion of the proteins was neutralized, dissolved in water, and spray-dried to yield a yeast protein isolate.

Product samples based on 1 kg. starting material (dry weight) were prepared with and without dialysis to show the effect of NaCl. The composition of the two primary products are summarized in Table I.

TABLE I
PRODUCT COMPOSITION

| Product | Dialysis | Ash, % | N, % | Protein, %* |
|---|---|---|---|---|
| Yeast Protein Isolate | − | 2.4 | 14.0 | 87.5 |
| Yeast Protein Isolate | + | 2.6 | 14.2 | 88.7 |
| Yeast Whippable Protein | − | 24.8** | 5.2 | 32.8 |
| Yeast Whippable Protein | + | 3.2 | 5.7 | 35.6 |

*(N × 6.25)
**Mainly NaCl

The product samples were further tested for their functional properties. These results are summarized in Tables II, III, IV, and V.

TABLE II
FOAMING AND EMULSIFYING PROPERTIES

| Product | Dialysis | Foaming Ability, ml.* | Foam Stability, ml.* | Emulsifying Capacity,** ml. oil/g. sample |
|---|---|---|---|---|
| Yeast Protein Isolate | − | 265 | 208 | 300 |
| Yeast Protein Isolate | + | 130 | 50 | 330 |
| Yeast Whippable Protein | − | 265 | 180 | 172 |
| Yeast Whippable Protein | + | 260 | 30 | 160 |

*Testing procedure on "Foaming Ability" and "Foam Stability": A 1 per cent aqueous solution of the test sample is agitated at 1000 rpm in a Virtis 45 mixer for 60 seconds at 32° F. The mixture is placed in a measuring cylinder and the measurement of volume in ml. is the "Foaming Ability." The foam is allowed to settle for 30 minutes, and the volume of foam remaining at that time, in ml., is the "Foam Stability."
**Testing procedure on "Emulsifying Capacity": A one g. sample of test material is mixed in a Waring blender with 50 ml. of a 0.9 per cent NaCl solution. 50 ml. of vegetable oil is added to the contents of the blender and mixed for ten seconds. A stream of oil is continuously added to the mixture at a rate of 20 ml./minute, with the blender mixing, until the emulsion breaks. The amount of oil added when the emulsion breaks is the "Emulsifying Capacity."

TABLE III
THERMOGELABILITY*

| Sample | Dialysis | Diameter, cm. | Height, cm. | Observations |
|---|---|---|---|---|
| Yeast Protein Isolate | − | 7.0 | 3.6 | cake, crystalline mild flavor, brown color |
| Yeast Protein Isolate | + | 7.0 | 4.1 | cake, crystalline, soft, mild flavor, cream color. |
| Yeast Whippable Protein | − | 12.8 | 0.9 | crystalline, brittle, tan color. |
| Yeast Whippable Protein | + | 13.2 | 0.8 | crystalline, crunchy. |
| Promosy 100 | − | 7.7 | 2.5 | soft, crystalline, tough, cream color. |
| Sodium caseinate | − | 9.0 | 2.5 | crystalline, tough, holes, cream color. |

*Testing procedure: Mix the following ingredients (given in weight per cent) into a ball and bake at 350° F. for 45 minutes:

| Protein sample | 10.00 |
|---|---|
| Salt | 0.75 |
| Sugar | 30.00 |
| Flour | 30.00 |
| Water | 25.25 |

Determine the dimensions, textures, and organoleptic properties.

TABLE IV
WHIPPABILITY IN FRAPPE SYSTEM*

| Product | Dialysis | Whippability | Color |
|---|---|---|---|
| Soy Isolate | − | Yes | White |
| Egg White | − | Yes | White |
| Yeast Protein Isolate | − | Yes (low volume) | Dark tan |
| Yeast Protein Isolate | + | Yes (low volume) | Slightly tan |
| Yeast Whippable Protein | − | Yes | White |
| Yeast Whippable Protein | + | Yes | White |
| Control | − | No | Slightly tan |

*Testing procedure: Heat corn syrup to 245° F. and add it to a slurry of invert sugar, water, and the protein sample. Beat in a Hobert mixer with whip for five minutes. Observe if foam is produced. The proportions of the ingredients are as follows (expressed as weight percent):
Corn syrup 47.3
Invert sugar 47.3
Water 3.6
Protein sample 1.8

TABLE V
PER CENT SOLUBIITY IN ACID pH*

| pH | Yeast Protein Isolate | Yeast Whippable Protein |
|---|---|---|
| 4.0 | 0 | 100 |

TABLE V-continued

| | PER CENT SOLUBIITY IN ACID pH* | |
|---|---|---|
| pH | Yeast Protein Isolate | Yeast Whippable Protein |
| 3.8 | 19.8 | 100 |
| 3.6 | 81.1 | 100 |
| 3.3 | 100 | 100 |

*One per cent of a protein sample in water was adjusted to the desired pH and dispersed for thirty minutes at room temperature. The suspension or solution was centrifuged for twenty minutes at 18,000 rpm. The concentration of nitrogen in the supernatant was determined and the percentageof soluble nitrogen calculated.

The results of these tests indicate that the yeast protein isolate appears to be responsible for the good emulsification characteristics and has about twice the emulsion capacity of soy isolate. In addition, the yeast protein isolate has thermogelability comparable to that of sodium caseinate. This property may be improved to some extent by mixing the yeast protein isolate with an amount of yeast whippable protein. In addition, the yeast whippable protein product is an excellent whippable protein material having a performance comparable to that of egg white. The functional performance of the yeast whippable protein product is not impaired by the high content of NaCl formed from neutralization. Furthermore, some hydrolyzed proteinaceous components were apparently lost through dialysis as indicated by the composition data in Table I. Hence, desalting is not necessary. Thus, the products produced by this process have the ability to replace the high-cost functional protein ingredients such as soy isolate, sodium caseinate, and egg white. Also, the yeast whippable protein is soluble at all acid pH values and the yeast protein isolate can be completely dissolved at pH 3.3. These properties demonstrate their potential for use in making acidic protein beverages.

It will be obvious to those skilled in the art that many variations from the preferred embodiment chosen for purposes of illustration can be made without departing from the scope of this invention.

I claim:

1. A process for preparing functional food yeast proteins comprising:
    (a) heating an aqueous slurry of whole yeast cells to an elevated temperature of from about 60° to about 100° C. to remove undesirable flavor and color bodies;
    (b) separating the yeast cells from the aqueous extract;
    (c) slurrying the separated yeast cells with a dilute alkaline solution having a pH of from about 8.5 to about 10.0 at a temperature of from about 85° to about 95° C. to remove nucleotidic materials;
    (d) separating the yeast cells from the alkaline extract;
    (e) reslurrying the separated yeast cells in a solution of about 0.1 to about 0.3 N sodium hydroxide or potassium hydroxide at a temperature of from about 85° to 100° C. to extract proteins;
    (f) neutralizing the slurry;
    (g) separating the undigested cell residue from the supernatant containing the extracted protein;
    (h) acidifying the supernatant to precipitate proteins at their isoelectric point;
    (i) separating the precipitated proteins from the mother liquor solution containing the soluble proteins;
    (j) neutralizing the mother liquor solution; and
    (k) drying the mother liquor solution to yield a yeast whippable protein.

2. The process of claim 1 wherein the precipitated proteins are neutralized and dried to yield a yeast protein isolate.

3. The process of claim 1 wherein the precipitated proteins are washed, neutralized, and dried to yield a yeast protein isolate.

4. The process of claim 1 wherein the separated cell residue of step (g) is washed with water which is combined with the supernatant prior to acidification.

5. The process of claim 1 wherein the mother liquor solution of step (k) is spray-dried.

6. The process of claim 1 wherein the supernatant of step (h) is acidified to a pH of from about 3.5 to 4.5.

7. The process of claim 1 wherein the separated yeast cells of step (e) are reslurried in a solution of 0.1 to 0.3 N sodium hydroxide.

8. The process of claim 1 wherein the food yeast is selected from the group consisting of *Candida utilis, Saccharomyces cerevisiae, Saccharomyces fragilis,* and *Saccharomyces carlsbergensis.*

9. A process for preparing functional food yeast proteins comprising:
    (a) heating an aqueous slurry of whole yeast cells to a temperature of from 60° to 100° C. to extract flavor and color bodies;
    (b) separating the yeast cells from the aqueous extract;
    (c) slurrying the separated yeast cells in a dilute alkaline solution having a pH of from about 8.5 to 10.0 at a temperature of from 85° to 95° C. to extract nucleotidic materials;
    (d) separating the yeast cells from the resulting alkaline extract;
    (e) reslurrying the separated yeast cells in a solution of from 0.1 to 0.3N sodium hydroxide at a temperature of from 85° to 100° C.;
    (f) neutralizing the slurry;
    (g) separating the undigested cell residue from the supernatant containing the extracted proteins;
    (h) acidifying the supernatant to a pH of from about 3.5 to 4.5 to precipitate proteins;
    (i) separating the precipitated proteins from the mother liquor solution containing the soluble proteins;
    (j) neutralizing the mother liquor solution to a pH of from 6.7 to 7.2; and
    (k) spray-drying the mother liquor solution to yield a yeast whipable protein.

10. The process of claim 9 wherein the precipitated proteins are dissolved in water by neutralization and spray-dried to yield a yeast protein isolate.

11. A process for preparing functional food yeast proteins comprising:
    (a) heating an aqueous slurry of from 10 to 14 weight percent (dry weight) of whole *Candida utilis* yeast cells to a temperature of about 95° C. for about from 1 to 5 minutes to remove flavor and color bodies;
    (b) separating the yeast cells from the aqueous extract;
    (c) slurrying the separated yeast cells in an alkaline solution having a pH of about 9.5 and a temperature of about 90° C. for from about 5 to 30 minutes to extract nucleotidic materials;
    (d) separating the yeast cells from the alkaline extract;
    (e) reslurrying the separated yeast cells in a 0.15N sodium hydroxide solution at a temperature of about 95° C. for from 15 to 45 minutes to extract proteins;

(f) neutralizing the slurry;

(g) separating the undigested cell residue from the supernatant containing the extracted proteins;

(h) acidifying the supernatant to a pH of about 4.0 to precipitate proteins;

(i) separating the precipitated proteins from the mother liquor solution containing the soluble proteins;

(j) neutralizing the mother liquor solution to a pH of about 7.0; and (k) spray-drying the mother liquor solution to yield a yeast whippable protein.

12. The process of claim 11 wherein the precipitated proteins are dissolved by neutralization in a solvent and spray-dried.

13. The process of claim 11 wherein the precipitated proteins are washed with water, dissolved in water by neutralization, and spray-dried.

14. The process of claim 11 wherein the precipitated proteins are washed with acetone, dissolved in water by neutralization, and spray-dried.

15. The process of claim 11 wherein the precipitated proteins are washed with ethanol, dissolved in water by neutralization, and spray-dried.

16. A process for preparing functional food yeast proteins comprising:

(a) slurrying whole yeast cells in a dilute alkaline solution having a pH of from about 8.5 to about 10 at a temperature of from about 85° to about 95° C. to extract nucleotidic materials and undesirable flavor and color bodies;

(b) separating the yeast cells from the alkaline extract;

(c) reslurrying the separated yeast cells in a solution of about 0.1 to about 0.3 N sodium hydroxide or potassium hydroxide at a temperature of from about 85° to 100° C. to extract proteins;

(d) neutralizing the slurry;

(e) separating the undigested cell residue from the supernatant containing the extracted protein;

(f) acidifying the supernatant to precipitate proteins;

(g) separating the precipitated proteins from the mother liquor solution containing the soluble proteins;

(h) neutralizing the mother liquor solution; and (i) drying the mother liquor solution to yield a yeast whippable protein.

17. The process of claim 16 wherein the precipitated proteins are dried to yield a yeast protein isolate.

18. The process of claim 16 wherein the precipitated proteins are washed, neutralized, and dried to yield a yeast protein isolate.

19. The process of claim 16 wherein the food yeast is selected from the group consisting of *Candida utilis, Saccharomyces cerevisiae, Saccharomyces fragilis,* and *Saccharomyces carlsbergensis.*

20. A process for preparing functional food yeast proteins comprising:

(a) slurrying whole yeast cells in a dilute alkaline solution having a pH of from about 8.5 to 10.0 at a temperature of from 85° to 95° C. for about from 5 to 30 minutes to extract nucleotidic materials and undesirable flavor and color bodies;

(b) separating the yeast cells from the alkaline extract;

(c) reslurrying the separated yeast cells in a solution of 0.1 to 0.3N sodium hydroxide at a temperature of from 85° to 100° C. for from 15 to 45 minutes to extract proteins;

(d) neutralizing the slurry;

(e) separating the undigested cell residue from the supernatant containing the extracted proteins;

(f) acidifying the supernatant to a pH of from 3.5 to 4.5 to precipitate proteins;

(g) separating the precipitated proteins from the mother liquor solution containing the soluble proteins;

(h) neutralizing the mother liquor solution to a pH of from 6.7 to 7.2; and (i) spray-drying the mother liquor solution to yield a yeast whippable protein.

21. The process of claim 20 wherein the precipitated proteins are dissolved by neutralization in a solvent and spray-dried to yield a yeast protein isolate.

22. The process of claim 20 wherein the food yeast is selected from the group consisting of *Candida utilis, Saccharomyces cerevisiae, Saccharomyces fragilis,* and *Saccharomyces carlsbergensis.*

23. The process of claim 20 wherein the food yeast is of the type *Candida utilis.*

24. The process of claim 23 wherein the precipitated proteins are dissolved by neutralization in a solvent and spray-dried to yield a yeast protein isolate.

* * * * *

UNITED STATES PATENT OFFICE
CERTIFICATE OF CORRECTION

Patent No. 4,079,048      Dated March 14, 1978

Inventor(s) Kwei C. Chao

It is certified that error appears in the above-identified patent and that said Letters Patent are hereby corrected as shown below:

| | |
|---|---|
| Column 4, line 62 | "invent" should be -- invert -- |
| Column 4, line 66 | "solubiity" should be -- solubility -- |
| Column 5, line 3 | "solubiity" should be -- solubility -- |
| Column 5, line 10 | "percentageof" should be -- percentage of -- |
| Column 6, line 49 | "whipable" should be -- whippable -- |

Signed and Sealed this

Twenty-second Day of May 1979

[SEAL]

Attest:

RUTH C. MASON  
Attesting Officer

DONALD W. BANNER  
Commissioner of Patents and Trademarks